United States Patent [19]

Boxhoorn et al.

[11] Patent Number: 4,701,437

[45] Date of Patent: Oct. 20, 1987

[54] ETHYLENE OXIDE CATALYST

[75] Inventors: Gosse Boxhoorn; Aan H. Klazinga; Otto M. Velthuis, all of Amsterdam, Netherlands

[73] Assignee: Shell Oil Company, Houston, Tex.

[21] Appl. No.: 874,924

[22] Filed: Jun. 16, 1986

[30] Foreign Application Priority Data

Jun. 28, 1985 [NL] Netherlands ............... 8501863

[51] Int. Cl.$^4$ ............ B01J 21/04; B01J 23/04; B01J 23/62; B01J 23/66
[52] U.S. Cl. ............ 502/348; 549/536
[58] Field of Search ............ 502/347, 348

[56] References Cited

U.S. PATENT DOCUMENTS 3,962,136  6/1976  Nielson et al. ............ 252/454
4,242,235 12/1980  Cognion et al. ............ 502/348 X Primary Examiner—W. J. Shine

[57] ABSTRACT

This invention relates to ethylene oxide catalysts comprising silver, alkali metal promoters supported on a carrier, which carrier is prepared by a process which comprises mixing an aluminum compound with a tin compound and calcining resultant mixture at a temperature greater than about 1100° C.

11 Claims, No Drawings

ETHYLENE OXIDE CATALYST

FIELD OF THE INVENTION

The invention relates to silver-containing catalysts suitable for the preparation of ethylene oxide and the process for preparing them and to the use of the catalyst for the preparation of ethylene oxide.

BACKGROUND OF THE INVENTION

It is generally known for a silver-containing catalyst to be employed in the preparation of ethylene oxide from ethylene. See for example U.S. Pat. No. 3,962,136 issued June 8, 1976, and also the literature cited therein. In order to obtain improved silver catalysts, efforts have been directed for many years towards modifying the silver catalysts with the aid of promoters. For example, the above-mentioned U.S. Pat. No. 3,962,136 describes a process in which to a carrier, after which the applied silver compound is reduced to silver and in which additionally a promoter in the form of potassium oxide, rubidium oxide or cesium oxide or a mixture thereof is present on the carrier. Commercially available silver catalysts are known under the brand names of Shell S809, S829 and S839.

SUMMARY OF THE INVENTION

The invention relates to a process for the preparation of a silver-containing catalyst suitable for the oxidation of ethylene to ethylene oxide, characterized in that a silver compound and, if desired, a promoter are applied to a carrier, after which the silver compound is reduced to metallic silver, and in which process the carrier has been prepared by mixing an aluminum compound with a tin compound and by calcining the resulting mixture. The catalysts thus prepared have a higher selectivity and a better dispersion of the silver particles on the surface of the carrier than catalysts prepared using conventional alpha alumina carriers.

DESCRIPTION OF THE PREFERRED EMBODIMENT

The aluminum compounds can preferably be modifications of aluminum oxide, which when calcined at between 1200° C. and 1700° C. can produce alpha-aluminum oxide, such as gamma-aluminum oxide. Another possibility is to use a hydrated alumninum oxide, such as boehmite, which on calcining at up to 1100° C. can produce gamma-aluminum oxide and on further calcining at temperatures of between 1200° C. and 1700° C. can produce alpha-aluminum oxide.

Some examples of tin compounds are tin salts such as stannic chloride, stannic bromide, stannic fluoride, stannic iodide, stannic nitrate, stannic sulphate, stannic tartrate, and stannic chromate. Salts of divalent tin are also suitable. Stannic sulphate is the most preferred. The quantity of tin compound mixed with the aluminum compound is preferably 1 to 30 w %, calculated on the weight of the aluminum compound (as $Al_2O_3$). Upon calcination tin will be in an oxidic form, possibly as a complex oxide.

It has been found that the Sn/Al atom ratio at the surface of the carrier is greater than the weighed-out Sn/Al atom ratio. It has also been found that the tin particles at the surface of the carrier have a great influence on the distribution of the metallic silver over the surface. It appears that if the catalyst is prepared according to the invention, the silver particles on the catalyst surface have a size of 0.08 m or even less, whereas the size of the silver particles on known commercial catalysts is 0.2–0.5 m. The particles on the catalyst prepared according to the invention are so small and so uniformly distributed that we can speak of a silver mirror on the surface of the carrier.

The catalysts according to the invention are, moreover, much more active than the commercial catalysts.

For the preparation of the made carrier, preferably an aluminum compound is mixed with water and the tin compound, the mixture thus obtained being extruded to shaped particles which are subsequently calcined. Calcination can take place in one or more steps, depending on the choice of starting material. In general, sufficient water is added to make the mixture extrudable. The extrudable paste obtained is then extruded in an extrusion press to form shaped pieces. These shaped pieces are heated, during which water still present is evaporated. The solid pieces are calcined at a temperature of between 1200° C. and 1700° C. Suitable starting materials are powders of gamma-aluminum oxide, alpha-aluminum oxide monohydrate, alpha-aluminum oxide trihydrate and beta-aluminum oxide monohydrate, which are sintered during the calcination, with fusion of the powder particles taking place.

The effective catalyst surface area can vary from between 0.2 and 5 $m^2/g$.

In order to prepare a catalyst, the made and modified carrier is impregnated with a solution of a silver compound sufficient to apply, as wished, 1 to 25 weight percent of silver, calculated on the weight of the total catalyst, to the carrier. The impregnated carrier is separated from the solution and the precipitated silver compound is reduced to silver.

Preferably, a promoter is added, for example one or more of the alkali metals: potassium, rubidium or cesium. The promoters can be applied to the carrier before, during or after the impregnation with silver compound. The promoter can also be applied to the carrier after the silver compound has been reduced to silver.

In general, the carrier is mixed with an aqueous solution of a silver salt or silver complex, so that the carrier is impregnated with this solution, after which the carrier is separated from the solution and subsequently dried. The impregnated carrier is then heated to a temperature of between 100° C. and 400° C. for a period necessary for the silver salt (or complex) to decompose and form a finely distributed layer of metallic silver which adheres to the surfaces. A reducing or inert gas can be passed over the carrier during the heating.

Various methods are known for adding the silver. The carrier can be impregnated with an aqueous solution of silver nitrate, then dried, after which the silver nitrate is reduced with hydrogen or hydrazine. The carrier can also be impregnated with an ammoniacal solution of silver oxalate or silver carbonate, the deposition of silver metal being effected by thermally decomposing the salt. Special solutions of a silver salt with certain solubilizing and reducing agents, such as combinations of vicinal alkanolamines, alkyldiamines and ammonia also serve the purpose.

The quantity of added promoter is generally between 20 and 1000 parts by weight of an alkali metal, such as potassium, rubidium or cesium (as metal) per million parts by weight of total catalyst. 50 to 300 parts by weight of alkali metal is particularly suitable. Suitable compounds to serve as starting material for promoters are, for example, nitates, oxalates, carboxylic acid salts or hydroxides. The most preferred promoter is cesium, the cesium being preferably employed as cesium hydroxide or cesium nitrate.

Some excellent methods are known for adding the alkali metals in which these metals can be applied at the same time as the silver. Suitable alkali metal salts are generally salts which are soluble in the silver-depositing liquid phase. Besides the above-mentioned salts, it is also worth mentioning nitrates, chlorides, iodides, bromides, bicarbonates, acetates, tartrates, lactates and isopropoxides. The use of alkali metal salts which react with the silver present in the solution and thus cause silver salts to be prematurely precipitated from an impregnating solution should, however, be avoided. For example, potassium chloride should not be used for impregnating techniques in which an aqueous silver nitrate solution is used, but potassium nitrate can be used instead. Potassium chloride can be suitably used in a process in which an aqueous solution of silver amine complexes, from which no silver chloride will precipitate, is used.

In addition, the amount of alkali metal deposited on the carrier can be adjusted within certain limits by washing out a part of the alkali metal with, preferably, anhydrous methanol or ethanol. This method is employed subsequently if the concentration of the applied alkali metal is found to be too high. The temperatures, contact times and the dry with gases can be adjusted. Care should be taken to ensure that no traces of alcohol remain in the carrier.

A preferably employed process consists of the carrier being impregnated with an aqueous solution containing both alkali metal salt and silver salt, the impregnating solution being composed of a silver salt of a carboxylic acid, an organic amine, a salt of potassium, rubidium or cesium and an aqueous solvent. For example, a potassium-containing silver oxalate solution can be prepared in two ways. Silver oxide can be reacted with a mixture of ethylene diamine and oxalic acid, giving a solution containing a silver oxalate ethylene diamine complex, to which a certain amount of potassium and possibly other amines such as ethanolamine is added. Silver oxalate can also be precipitated from a solution of potassium oxalate and silver nitrate, the silver oxalate thus obtained then being repeatedly washed in order to remove the attached potassium salts until the desired potassium content is obtained. The potassium-containing silver oxalate is then solubilized with ammonium and/or amine. Solutions containing rubidium and cesium can also be prepared in this way. The thus impreganted carriers are then heated to a temperature 100° C. and 400° C., preferably between 125° C. and 325° C.

It should be noted that, irrespective of the nature of the silver in the solution before the precipitation onto the carrier, reference is also made to reduction to (metallic) silver, whereas it could also be referred to as decomposition on heating. It is preferred to think in terms of reduction, since positively charged Ag ions are converted into metallic Ag. The reduction times can be simply adapted to the starting materials employed.

As mentioned above, a promoter is preferably added to the silver. Cesium is the most preferred promoter in view of the fact that its selectivity for ethylene oxide has been found to be the highest in comparison with the use of potassium or rubidium as promoter.

Thus, the preferred catalyst comprises about 1-25 w % of silver (basis total catalyst) and about 20-1000 ppm metal, (measured as the metal, basis total catalyst) of an alkali metal promoter selected from potassium, rubidium, cesium and mixtures thereof supported on a carrier, which carrier is prepared by process which comprises mixing an aluminum compound, preferably boehmite and/or gamma alumina, with a tin compound, wherein the quantity of tin compound is about 1-30 wt % calculated on the weight of the aluminum compound (as $Al_2O_3$), then calcining the resultant mixture at a temperature greater than about 1100° C., preferably between about 1200° C. and about 1700° C. In a preferred embodiment water is also added to the mixture which is then extruded and calcined.

The silver catalysts prepared by the process according to the present invention appear to be particularly active catalysts for the direct catalytic oxidation of ethylene to ethylene oxide with the aid of molecular oxygen. The conditions for carrying out the oxidation reaction in the presence of the silver catalysts according to the invention are fairly similar to those already described in the literature. This applies to, for example, suitable temperatures, pressures, residence times, diluents such as nitrogen, carbon dioxide, steam, argon, methane or other saturated hydrocarbons, the presence or absence of moderating agents to control the catalytic action, for example 1,2-dichloroethane, vinyl chloride or chlorinated polyphenyl compounds, the desirability of employing either recirculating treatments or successive conversions in different reactors to enhance the yield of ethylene oxide, as well as any other special conditions which may be chosen for processes for the preparation of ethylene oxide. Usually, the pressures employed vary from about atmospheric pressure to about 35 bar. Higher pressures are, however, by no means excluded. The molecular oxygen employed as reactant can be obtained from conventional sources. The oxygen supply can consist substantially of relatively pure oxygen, a concentrated oxygen stream consisting of a large amount of oxygen with smaller amounts of one or more diluents, such as nitrogen, argon, etc., or another oxygen-containing stream, such as air.

In a preferably employed application of the silver catalysts according to the present invention, ethylene oxide is prepared by contacting an oxygen-containing gas that has been separated from air and that contains not less than 95% oxygen with ethylene in the presence of the catalysts in question at a temperature within the range of 210° C. to 285° C. and preferably between 225° C. and 270° C.

In the reaction of ethylene with oxygen to ethylene oxide, the ethylene is present in at least a double molecular quantity, but the quantity of ethylene employed is generally much higher. The conversion is therefore calculated according to the quantity of converted oxygen in the reaction and we therefore speak of oxygen conversion. This oxygen conversion is dependent on the temperature of the reaction and is a measure of the activity of the catalyst. The values $T_{30}$, $T_{40}$ and $T_{50}$ refer to the temperatures at 30 mol %, 40 mol % and 50 mol % conversion respectively of the oxygen in the reactor. The temperatures are generally higher for a higher conversion and are highly dependent on the catalyst employed and the reaction conditions. In addition to these T-values, one also comes across selectivity values, which indicate the mol % of ethylene oxide in the reactant mixture obtained. The selectivity is indicated as $S_{30}$, $S_{40}$ or $S_{50}$ which refers to the selectivity at 30%, 40% or 50% oxygen conversion respectively.

The invention is illustrated by the following examples which are provided for illustration and are not to be construed as limiting the invention.

EXAMPLE 1

6.1 g stannic sulphate in 160 ml water was mixed with 133.3 g Kaiser aluminum oxide (26405) ($Al_2O_3 \cdot H_2O$) by adding stannic sulphate in water to aluminum oxide, and the mixture was kneaded for 8 minutes in a masticator. The paste obtained was then extruded. The resulting shaped pieces were dried at 120° C. and subsequently calcined at progressively higher temperatures. Calcination was started with the temperature rising at a rate of 200° C./h up to 500° C. Calcination was then continued for 1 hour at 500° C., after which the temperature was raised in 2 hours to 1400° C. Finally, calcination was continued for 1 hour at 1400° C. The pore volume of the shaped pieces was 0.45 ml.g$^{-1}$ and the average pore diameter was 1.0 µm. The tin/aluminum ratio at the surface is greater than the weighed-out tin/aluminum ratio. The resulting shaped pieces were impregnated with an aqueous solution of silver oxalate to which cesium hydroxide was added. The impregnation was carried out for 10 minutes under vacuum, after which the shaped pieces were separated from the solution and placed in a hot air stream at a temperature of 250–270° C. for 10 minutes in order to convert the silver salt to silver. The aqueous solution of silver oxalate was a 28 wt % Ag-containing aqueous solution in which the silver oxalate was complexed with ethylene diamine and to which solution cesium hydroxide was added. After the hot air treatment the thus impregnated shaped pieces contained 21 wt % Ag (calculated on total catalyst) and 480 parts by weight of cesium per million parts by weight of total catalyst.

The catalyst obtained was then used for the preparation of ethylene oxide from ethylene and oxygen. A cylindrical steel reactor with a length of 40 cm and a cross-section of 5 mm was filled entirely with catalyst particles of about 1 mm in size. The reactor was placed in a bath in which silicon oxide and aluminum oxide particles were present in a fluidized bed. A gas mixture with the following composition was passed through the reactor: 30 mol % ethylene, 8.5 mol % oxygen, 7 mol % carbon dioxide, 54.5 mol % nitrogen and 5.5 parts per million parts of gas of vinyl chloride as moderator. The space velocity was 3300 l.l$^{-1}$.h$^{-1}$. The pressure was 15 bar and the temperature was dependent on the set oxygen conversion. The measuring equipment was connected to the reactor and to a computer such that the conversation and the temperature could be accurately controlled. The concentrations of the reaction components were determined with the aid of gas chromatography and mass spectrometry. After 24 h the reaction temperature was measured at 40% oxygen conversion and found to be 212° C.

A similar test with the standard S839 catalyst utilizing a conventional alpha aluminum carrier gave a $T_{40}$ of 236° C. It appeared, therefore, that the silver-containing catalyst according to the invention had a $T_{40}$ which was 24° C. lower than the $T_{40}$ of the standard catalyst S839 under the same reaction conditions.

EXAMPLE 2

A silver-containing catalyst prepared in the same way as in Example 1, but in which 5 times as much stannic sulphate was used in the carrier preparation, and which catalyst contained 18 wt % silver and 290 ppm cesium, was tested at 50% oxygen conversion. The size of the silver particles on the catalyst was 60 nanometer (nm). The reaction conditions were the same as in Example 1, except that the gas mixture passed into the reactor contained no carbon dioxide.

It appeared that this silver-containing catalyst according to the invention had a $T_{50}$ which was 17° C. below the $T_{50}$ of the standard catalyst S839 under the same reaction conditions.

It also appeared that the surfaces of the catalysts prepared by means of the process according to Examples 1 and 2 were almost entirely covered by silver particles (found with the aid of electron microscopy and scanning auger electron spectroscopy).

We claim:

1. A catalyst for the production of ethylene oxide from ethylene and molecular oxygen which comprises silver and an alkali metal promoter supported on a carrier, which carrier is prepared by a process which comprises mixing an aluminum compound with water and a tin compound and calcining the resultant mixture at a temperature between 1200° C. and 1700° C.

2. The catalyst of claim 1 wherein the aluminum compound is an aluminum oxide or a hydrate of aluminum oxide.

3. The catalyst of claim 1 wherein the tin compound is a compound which upon calcination is converted to an oxidic form.

4. The catalyst of claim 1 wherein the tin compound is stannic sulphate.

5. The catalyst of claim 1 wherein the aluminum compound is mixed with a tin compound such as that the quantity of tin compound is about 1–30 wt % calculated on the weight of the aluminum compound (as $Al_2O_3$).

6. The catalyst of claim 1 wherein the aluminum compound is boehmite or gamma-aluminum oxide.

7. The catalyst of claim 1 wherein the silver comprises about 1 to about 25 wt %, calculated on the weight of the total catalyst and the alkali metal promoter comprises about 20 to about 1000 parts by weight of the alkali metal (measured as the metal) per million parts by weight of the total catalyst.

8. A catalyst for the production of ethylene oxide from ethylene and molecular oxygen which comprises about 1–25 wt % silver (basis total catalyst) and about 20–1000 ppm (measured as the metal, basis total catalyst) of an alkali metal promoter supported on a carrier, which carrier is prepared by a process which comprises mixing an aluminum compound with water and a tin compound wherein the quantity of the tin compound is about 1–30 wt % calculated on the weight of the aluminum compound (as $Al_2O_3$), and calcining the resultant mixture at a temperature between about 1200° C. and about 1700° C.

9. The catalyst of claim 8 wherein the alkali metal promoter is selected from the group consisting of potassium, rubidium, cesium and mixtures thereof, the aluminum compound is selected from the group consisting of boehmite, gamma alumina, and mixtures thereof and the tin compound is stannic sulfate.

10. A catalyst for the production of ethylene oxide from ethylene and molecular oxygen which comprises about 1–25 wt % silver (basis total catalyst) and about 20–1000 ppm (measured as the metal, basis total catalyst) of an alkali metal promoter supported on a carrier, which carrier is prepared by process which comprises mixing boehmite and/or gamma aluminum, water, and a tin salt wherein the quantity of the tin compound is about 1–30 wt % calculated on the weight of the aluminum compound (as $Al_2O_3$), with the resulting mixture being extruded to shape the catalyst particles which are then calcined at a temperature between about 1200° C. and about 1700° C.

11. The catalyst of claim 10 wherein the alkali metal promoter is selected from the group consisting of potassium, rubidium, cesium and mixtures thereof and the tin compound is stannic sulphate.

* * * * *